(12) United States Patent
Azzaro et al.

(10) Patent No.: US 7,540,841 B2
(45) Date of Patent: Jun. 2, 2009

(54) SYSTEM AND METHOD FOR IN-SITU MENTAL HEALTH MONITORING AND THERAPY ADMINISTRATION

(75) Inventors: Steven Hector Azzaro, Schenectady, NY (US); Christopher Donald Johnson, Clifton Park, NY (US); Virginia Ann Zingelewicz, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/611,355

(22) Filed: Dec. 15, 2006

(65) Prior Publication Data

US 2008/0146888 A1    Jun. 19, 2008

(51) Int. Cl.
    *A61B 5/00*    (2006.01)
(52) U.S. Cl. .......................................... 600/300; 607/2
(58) Field of Classification Search .................. 600/300
    See application file for complete search history.

(56) References Cited

U.S. PATENT DOCUMENTS

| | | | |
|---|---|---|---|
| 5,918,603 A * | 7/1999 | Brown | 128/897 |
| 6,186,145 B1 * | 2/2001 | Brown | 128/897 |
| 6,625,485 B2 * | 9/2003 | Levendowski et al. | 600/544 |
| 6,985,870 B2 * | 1/2006 | Martucci et al. | 705/3 |
| 7,054,758 B2 * | 5/2006 | Gill-Garrison et al. | 702/20 |
| 2005/0165458 A1 | 7/2005 | Boveja et al. | |
| 2005/0245790 A1 | 11/2005 | Bergfalk et al. | |
| 2005/0261542 A1 | 11/2005 | Riehl | |
| 2006/0058856 A1 | 3/2006 | Morrell | |
| 2006/0079936 A1 | 4/2006 | Boveja et al. | |
| 2006/0111690 A1 | 5/2006 | Hildebrand | |

FOREIGN PATENT DOCUMENTS

| | | |
|---|---|---|
| WO | WO0047108 | 8/2000 |
| WO | WO2005017203 A2 | 2/2005 |
| WO | WO2006056907 | 6/2006 |
| WO | WO2006119186 | 9/2006 |

OTHER PUBLICATIONS

PCT Search Report—May 28, 2008.

* cited by examiner

*Primary Examiner*—Thor S Campbell
(74) *Attorney, Agent, or Firm*—Jenifer E. Haeckl

(57) ABSTRACT

Method and systems for diagnosing and treating individuals having a mental health disease that provide health related information about one or more of the individuals wherein at least portion of the information comprises collected data on one or more of the individual's activities; analyzes the health related information according to assess the individual's mental health; and creates a treatment plan based at least in part on the individual's assessed state of mental health.

16 Claims, 3 Drawing Sheets

SYSTEM AND METHOD FOR IN-SITU MENTAL HEALTH MONITORING AND THERAPY ADMINISTRATION

BACKGROUND

The invention relates generally to methods and systems for monitoring an individual's activities to determine their relative state of mental health in terms of propensity of depression and/or mental agility and suggesting the protocol driven therapies in accordance to their state of mental health relative to desired metrics.

Mental health such as that associated with depressed or with patients loosing mental acuity is currently treated through healthcare provider interactions such as physician and psychologist visits and resultant medication and mental exercise recommendations, followed by no direct patient-doctor interaction until the next visit. Even when a visit occurs, the healthcare provider is primarily dependent on the patient or an observer of the patient to relate and summarize changes in capability, habits and moods. A system that would monitor appropriate behaviors and either automatically adjust medication or present the data such that medication adjustments could be made in the context of a protocol in a more timely manner will help sufferers of depression anxiety, and loss of mental acuity.

BRIEF DESCRIPTION

The methods and systems utilize information regarding changes in an individual's patterns of activity, sleep, eating, media viewing, response to media and other types of the ubiquitous activities of daily living to determine that individual's state of mental health and, in one or more of the embodiments, more specifically, that individual's level of depression or mental acuity. The information provided, or gathered through a monitoring system, is used at least in part as a basis for measuring the relative mental health state of a patient, assessing the relative state to a desired state, administering medications, and adjusting medication levels and the frequency at which medications and other therapies such as physical activity, media programming and interactivity and decision point behavior such as that associated with financial activity are administered. Caregivers may also use the methods and systems, if feasible in a given situation, to administer medications using a pharmaceutical patch or another means of administration that does not necessarily require patient initiated compliance.

The technical effect of the methods and systems is to enable caregivers and individuals to: collect objective data with minimal patient inconvenience; to correlate patterns and changes in the data to an individual's state of mental health; and to regulate and, if necessary, change the individual's medication or other therapy regime based on patterns in the data and changes in the individual's types, responses and level of activities. The overall result is more diagnostic clarity for the healthcare provider and a much more positive outcome for the patient from the active feedback mechanisms that are enabled with the present invention.

For example, the methods and systems provide a more effective vehicle for understanding, measuring on a relative basis over time, diagnosing and treating mental disorder. Up until now, diagnosis of mental health relied exclusively on verbal and visual interaction between the physician and patient, actively questioning the patient about their status or state of mental health or relying on the patient to assess his or herself and raise concerns based on the patient's subjective assessment. Alternatively, an observer such as a family member or caregiver provides summary data gleaned from discrete observations.

One or more of the embodiments of the methods and systems are suited to improving the quality of life and productivity of individuals who suffer from depression, as well as those who care for them. Depression, when detected, is also an important indicator of other types of medical non-compliance. A ubiquitous, low cost, activity measure and therapeutic control path is desirous.

An embodiment of a method for diagnosing and treating individuals having a mental health disease generally comprises the steps of: providing health related information about one or more of the individuals wherein at least a portion of the information comprises collected data on one or more of the individual's activities; analyzing the health related information to assess the individual's absolute and relative mental health, and creating a treatment plan based at least in part on the individual's assessed state of mental health. The system may be configured to automatically act on the plan or to transmit a proposed plan to a caregiver who may make the decision whether to act in whole or in part on the plan. The system may also be configured to transmit the data to a caregiver who may, in turn, generate the plan and decide whether to act on a plan in whole or in part. The analyzing step is preferably automated using a computer-based protocol. The activity data may comprise a variety of data on the individual's daily activities such as, but not limited to, sleep pattern data and general activity level and media viewing and response data. The health related information may comprise but is not limited to mental health related information, the individual's mental health history, and/or physiological measurements.

The method may further comprise the steps of providing a means for passively administering one or more medications or therapies directly to the individual, automatically triggering the means for passively administering one or more medications, and/or transmitting the treatment plan to the individual over a computer or media network relative to a protocol of care that a healthcare provider establishes.

An embodiment of a system monitoring and treating individuals having a mental health disease generally comprises: a means for at least temporarily storing health related information about one or more of the individuals wherein at least a portion of the information comprises data on one or more of the individual's activities; the ability to incorporate some or all data or summarization in an electronic medical record, the ability to integrate with financial records, a processor for analyzing the health-related information to assess the individual's mental health; and a manual interpersonal or automated device for generating a treatment plan based at least in part on the individual's assessed mental health. The system may further comprise a monitoring system for sensing one or more activities of the individual; wherein the monitoring system comprises one or more sensors, such as a motion or pressure sensor or device for recording electronic or digital based activity such as media viewing or interactivity, Internet usage or other computer based activities including but not limited to financial transactions, website visits and incoming and outgoing emails. The system may still further comprise a means for transmitting data corresponding to the sensed activities to a remote location; and/or a means for transmitting at least part of the treatment plan to the individual, caretaker, or healthcare professional, wherein the means may comprise a computer network or media channel or delivered media such as a network, cable or mobile show.

One or more of the activities may be selected from a group of activities consisting of: sleeping, activating or deactivating an in-home device, entering or leaving a living area of the individual, exercising, making sounds, physical movement by the individual, opening or closing a door or window, using a computer or other electronic digital devices, website usage, making financial relating transactions and selecting or using media. The activities are not necessarily limited to these specific activities and may include any activity that is indicative of a person's mental state of health.

The health related information may comprise, but is not limited to, one or more types of information selected from a group consisting of: data on motion in a user area, financial related transaction data, media use data, and media interaction data; and still further comprise credit related data. The health related information used in the system, may also comprise two or more of these types of information selected from the group. The assessment of mental health may comprise an analysis of an absolute measure and a relative measure of mental acuity; and if desired, more specifically an analysis of an absolute and a relative measure of depression.

If the individual utilizes a passive device for administering one or more medications, the system may comprise a means for activating the passive device, wherein the means for activating comprises a radio frequency or infrared signal or embedded audio or video pattern.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Mental health diseases, including but not limited to depression, are difficult to treat. Many aspects of an individual's health, personal life and outside factors can impact the severity of mental diseases. Measuring the diseases's acuity at the time and place of occurrence and treating it with medication or by means of stimulating the body's naturally occurring favorable response mechanisms are important to the patient's overall recovery and success. The technical effect of the methods and systems is, in part, to monitor and analyze patients' activities to enable more effective treatment through the increased precision, trending, timeliness of, and response to, physiological and medication therapy.

Figure 1:
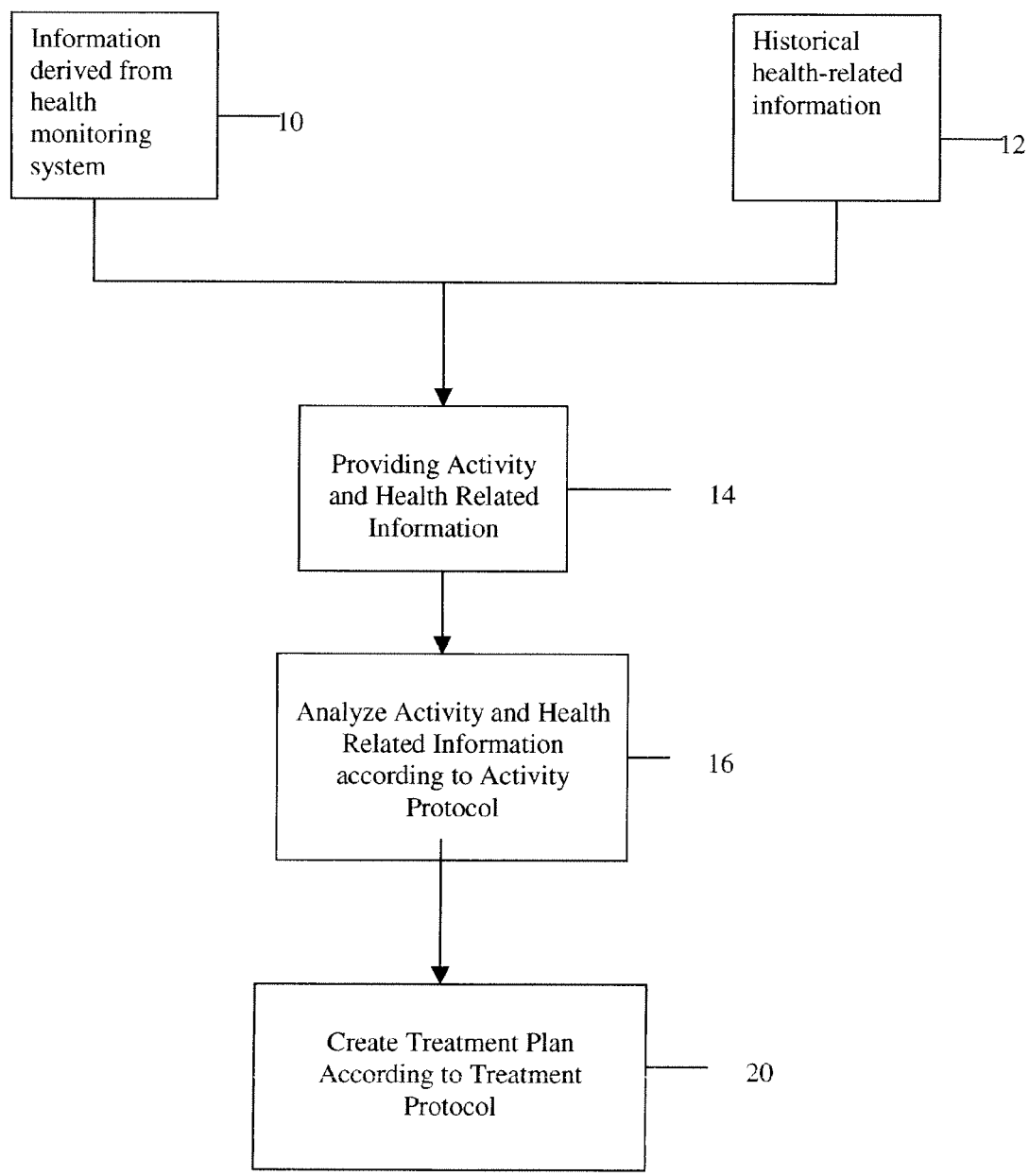
FIG. 1 is a block diagram of an embodiment of the system for monitoring and diagnosing mental state.

One embodiment of the method, as shown in FIG. 1, for monitoring the types and levels of an individual's daily activities and using data that reflects this activity to determine the individual's state of mind and more specifically their mental health, and to treat or otherwise regulate their mental health, generally comprises the steps of providing health related information 14, such as personal monitored activity related data 10 or historical health-related information 12 about an individual; analyzing, in step 16, the individual's information to assess the individual's state of mind or mental health; and creating a treatment plan 20 that addresses the individual's assessed mental health. The activity data, and any other related or relevant information, may be analyzed using a logical tree such as an activity-based protocol to assess either manually or automatically, what is the patient's state of mind or mental health. Still further, a treatment protocol may be used to change or create a treatment plan to address the patient's mental health. The activity-related data 14 and any other related or relevant information, may be derived from information or data gathered by a the monitoring system in step 10 or from personal health related information about the individual in step 12. A health care provider, in step 16, analyzes that information, either manually or using an automated subsystem, to assess the individual patient's state of mind and mental health. The analytical steps of the methods and systems may be automated using one or more computer assisted decision protocol that are based at least in part on the type and level of activities of the individual patient. Other personal information about the individual, such as, but not limited to, mental history, family history, physiological measurements, current and past measurements, medication regimes and responses, daily routine and physical health, may also be used and incorporated into the activity based protocol and/or the treatment protocol.

The methods and systems used to monitor the type and level of an individual's activities are preferably incorporated into the individual's living environment, areas and activities. The monitoring system senses and records activities that may be in the methods and systems as proxies or indicators for mental health diseases such as, but not limited to, depression and mental acuity. Sensing specific indicators of mental diseases, such as depression, in an individual's in situ living area is a marked improvement over current methods that require a patient to travel to a clinical setting. Not only is travel time obviated, the measured indicators will be more accurate and less contrived. The method and system utilizes a modality that can co-exist with the patient's daily routine. The mechanism's utility is further enhanced with the collection of time series data for temporal patterns.

The individual's mental health-related information is generated from data gathered through a system that monitors one or more activities of the individual in one or more living areas of the individual or activities of the individual. This information may be used to generate at least part of the mental health-related information based on the activity of the individual. The health-related information can be transmitted to health care providers who are responsible for assessing and treating the individual patient's mental health with direct personal intervention or with the benefit of decision support or automated therapy.

Figure 2:
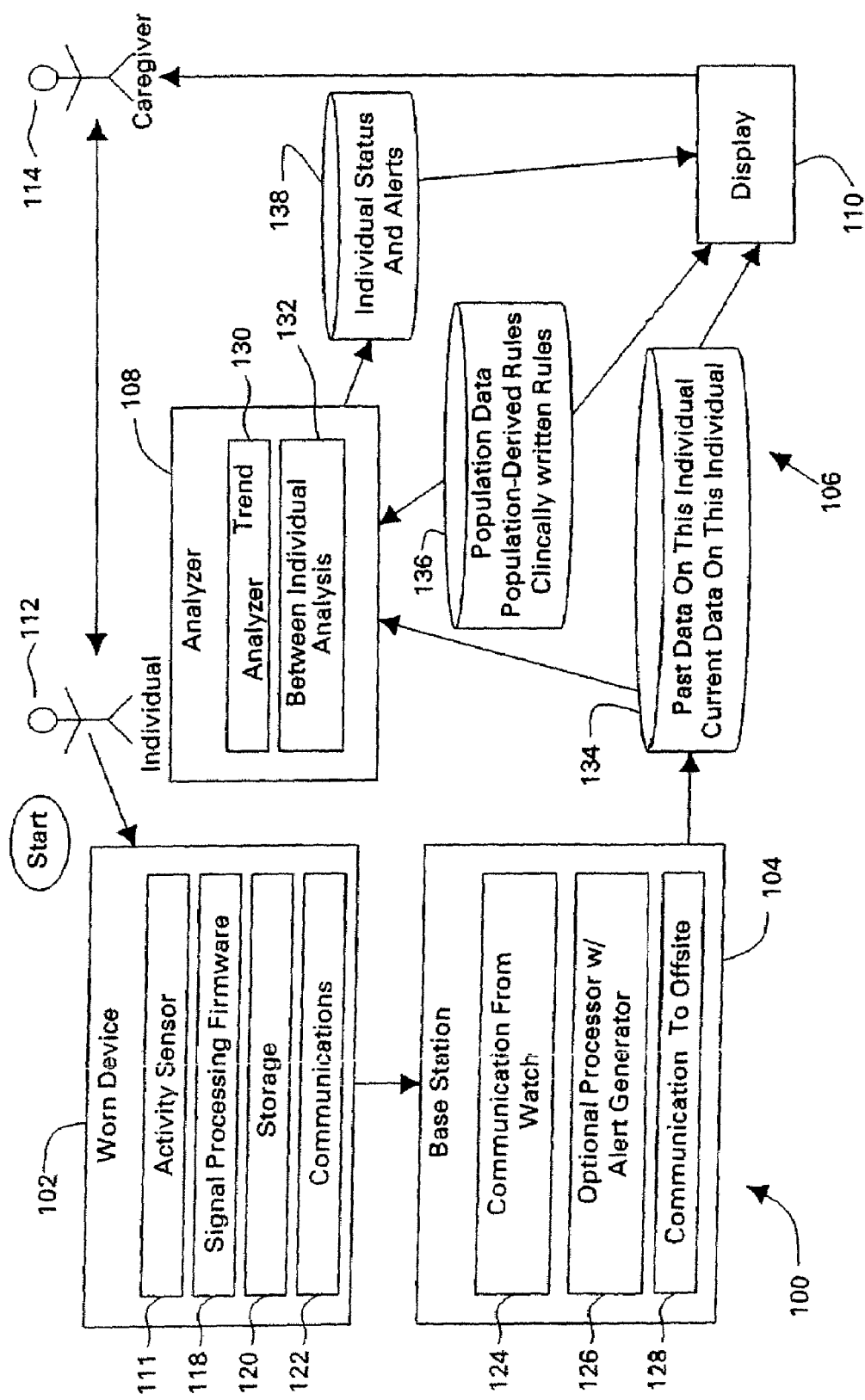
FIG. 2 is a block diagram of an embodiment of the mental health monitoring system for obtaining mental health related information about an individual for use in the system of FIG. 1.
Figure 3:
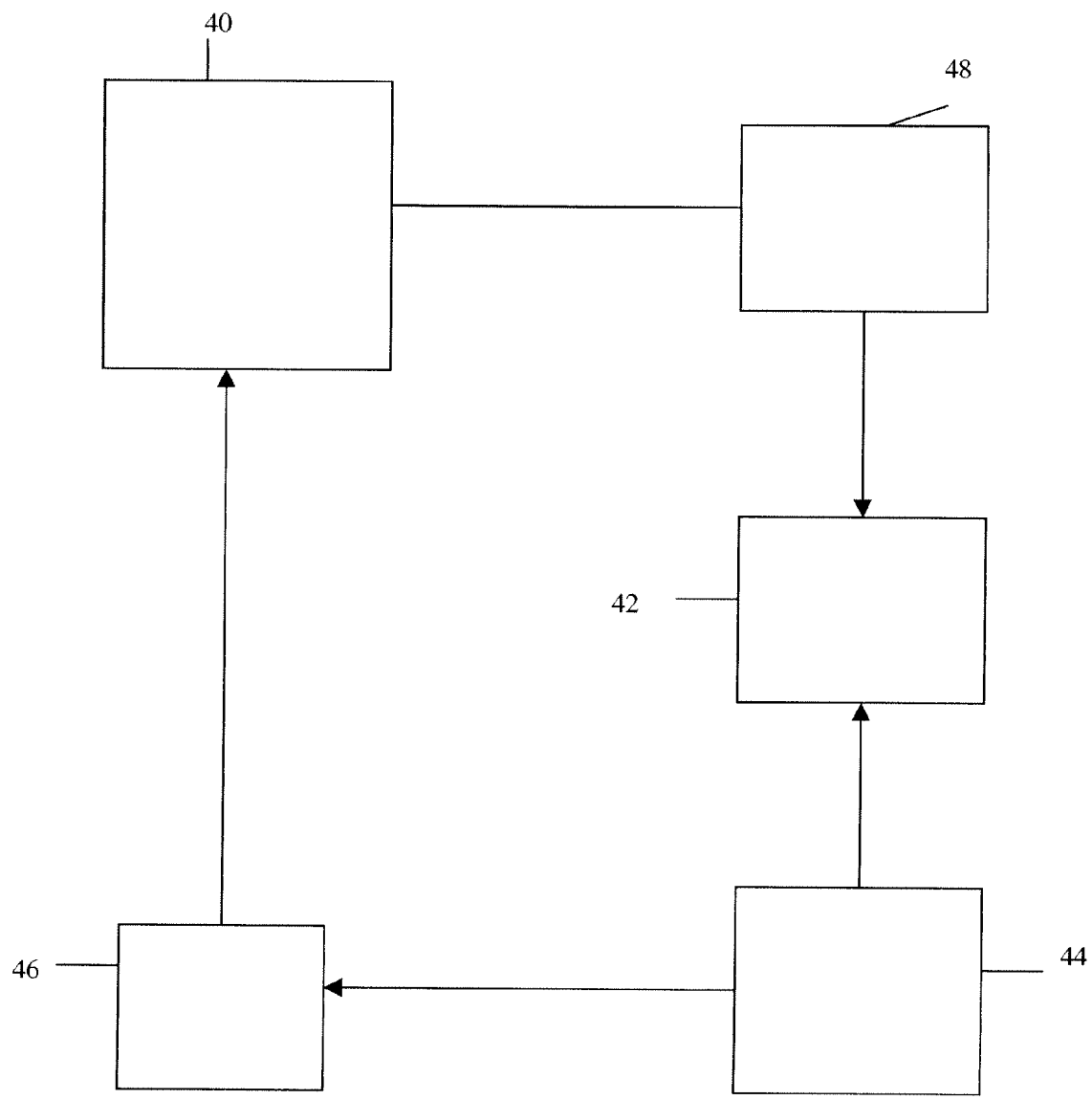
FIG. 3 is a block diagram of an embodiment of a subsystem for applying a treatment plan to an individual.

An embodiment of such a system for monitoring an individual's activities and gathering health related information, is shown and generally referred to in FIG. 2 as system 100. System 100 comprises one or more personal devices 102, one or more hubs or base stations 104, one or more local or remote databases 106, and one or more local or remote processors 108. Such remote databases or processors may reside in or otherwise communicate with monitoring center 44. Monitoring center 44 may be configured to be accessible by the individual or authorized caregivers through the Internet or any other suitable wired or wireless means. Device 102 preferably comprises a display 110. Although device 102 is shown in FIG. 2 as a user-wearable, non-encumbering device, device 102 is not limited to a worn device and may comprise any number and type of devices suitable for sensing one or more activities or physiological indicators that are relevant to health-related information. Examples include, but are not limited to, media viewing, interactivity and financial consumer credit activity. Device 102 comprises an activity and/or a movement sensor 111 that substantially, continuously monitors and collects the daily-activity data of user 112. Processor 108 may be embodied within device 102, base station 104 and/or a remotely located processing system. The data collected by device 102 may be directly analyzed by processor 108 if housed within device 102 or the data may be transmitted to base station 104 or a remote processor where a caregiver is located. The data may be transmitted wirelessly or by hardwire.

System 100 may also comprise one or more sensors in addition to the sensor embodied within device 102. A plurality of sensors may be positioned throughout the living area to monitor the individual's more specific activities such as sleeping, exercising, watching television or cooking. Further, device 102 or one or more of the sensors may further comprise or include a device that is adapted to measure activity related to financial activity culled, for example, from consumer credit and banking records. Device 102 or one or more other devices may be configured to record electronic or digital based activity such as media viewing or interactivity, Internet usage or other computer based activities including but not limited to financial transactions, website visits, keystrokes and incoming and outgoing emails.

One or more of the activities include, but are not necessarily limited to, sleeping, activating or deactivating an in-home device, entering or leaving a living area of the individual, exercising, making sounds, physical movement by the individual, opening or closing a door or window, using a computer or other electronic digital devices, website usage, making financial relating transactions and selecting or using media. The activities are not necessarily limited to these specific activities and may include any activity that is indicative of a person's mental state of health.

The health related information may comprise, but is not limited to, one or more types of information selected from a group consisting of: data on motion in a user area, financial related transaction data, media use data, and media interaction data; and still further comprise credit related data. The system may use any number and types of health related information and data on activities in the assessment and generation of a treatment plan. The assessment of mental health may also comprise an analysis of an absolute measure and a relative measure of mental acuity; and if desired, more specifically an analysis of an absolute and a relative measure of depression.

If the processor in the device, base station, or remote monitoring center makes a determination from the daily or temporal activity data of individual 112 that a change in of the activity level of individual 112 has occurred, the processor generates an indication of the change for further analysis or access by a remote caregiver 114. The remote caregiver 114 may be presented trends over hours, days and/or weeks to determine what, if any, change in treatment is needed. The system may be configured to analyze the data and create a treatment plan automatically using the protocols of the methods.

Device 102 allows individual 112 to move about the living or relevant activity area unencumbered while device 102 unobtrusively, automatically and continuously monitors and collects daily-activity data associated with individual 112. As noted, device 102 may be configured to house a movement sensor 111 and one or more of signal processing firmware 118, storage 120, transmitter 122, a sensor to determine whether the device is being worn or not worn, and/or processor 108. The sensor to determine whether the device is being worn may comprise a temperature sensor and/or magnetic, sound, vibration, electrical or light based contact/circuit sensors. Device 102 may be configured to monitor movement, acceleration, vibration, sound and/or change in orientation. For example, device 102 may comprise one or more of an accelerometer, actigraph, pendulum-based pedometer, tilt switch, vibration sensor, location sensor (e.g. calculates distance traveled), and/or motion detector. Device 102 may be configured to monitor activity such as viewing media, interactions with media content and financial activity such as banking and consumer credit transactions.

Device 102 is preferably capable of measuring activity levels over twenty-four hour periods for a relatively long-term duration. If desired, device 102 may be configured to measure one or more physiological parameters of individual 112, such as temperature, blood pressure, heart rate and blood sugar, as well.

Device 102 may be housed or otherwise embodied in any convenient, but comfortable, wearable accessory such as, but not limited to, wristbands, wrist or pocket watches, necklaces, pendants and bracelets. Device 102 preferably comprises a data collection means that comprises signal processing firmware 118 and/or storage device 120.

As noted, the analytical steps of the methods and systems may be automated using one or more computer assisted decision protocols that are based at least in part on the type and level of activities of the individual patient, as well as other personal information about the individual. Any or all of this information may also be used and incorporated into the activity based protocol and/or the treatment protocol. The activity protocol may utilize one or more activities as indicators of various mental diseases including, but not limited to, depression and mental acuity. A few examples of such indicators of depression and mental acuity include, but are not limited to:

1. Exhaustion upon waking
2. Disrupted sleep, sometimes through upsetting dreams
3. Early morning waking and difficulty getting back to sleep
4. Doing less of what they used to enjoy
5. Difficulty concentrating during the day
6. Improved energy as the day goes on
7. Anxious worrying and intrusive upsetting thoughts
8. Becoming emotional or upset for no particular reason
9. Shortness of temper, or irritability
10. Declining inquisitiveness in media viewing patterns or interaction patterns as provided
11. Emotional buying or redundant buying in financial transactions such as purchases Indicators 2 and 3 from the list above can be directly observed through sensor-based systems such as the monitor system 100. For example, sleep patterns may be monitored using passive infrared motion detectors or pressure or sound sensors located near or on the individual's bed. Any number of daily activities may be monitored using actigraphy devices such as actigraphy watches, which enable detailed assessment of active and sleep states. Sensors may be placed throughout the individual's living areas or in select locations, depending on the activities that need to be monitored. Manual or automated devices may be used to measure various physiological parameters such as weight, temperature, blood pressure, and pulse. These devices may be incorporated into the automated system 100 and their respective measured parameters automatically transmitted to a care giver. The device may also be manual if, for example, lower cost or greater privacy is desired by the individual.

Other indicators of depression or other mental diseases may be derived from the individual's activities. For example, energy improvement indicator 6 may be derived directly from an individual's overall activity level. Exhaustion upon waking indicator 1 may be derived from decreased activity level immediately after waking. Increases in the amount of time at home may indicate that someone was doing less of what they enjoyed as with indicator 4.

The other five example indicators listed, 5 and 7-10, may be derived through media enabled interaction. For example, one embodiment uses manual (electronic such as web-based or phone) interaction in instances in which other parameters indicate a need for greater precision. Additionally, indicator 5 may be observed or derived based on the individual's use of, or change in use of, media and/or media-based content such as computer games, email, Internet usage, broadcast television, cable, satellite, telephone/cellphone use or any other type of activatable device. Such devices may be stand alone or collaborative gaming or content development based devices. The methods and systems may also be configured to measure biometrical responses and to monitor informational events such as financial activity as detected through the analysis of transactions.

Mental acuity may also be derived from monitored activities. For example, when the patient is exposed to content, the individual's mental acuity may be determined based on their interactions with that content. Further, mental exercise, proportional and in relationship to the responses to the content and the patient's protocol may also be enabled interactively. Response time constants and retention tests are examples of information that may be monitored and collected. Indicators 5, 8, 9 and 10 may be derived from observations made during content delivery such as TV or other entertainment viewing. As noted, other in-situ measurements may be collected, such as but not limited to, pulse, rate of change of skin surface temperature, change of skin surface resistance blood pressure, blood sugar, and hormone levels using biometrical apparatus-provided metrics (such as, but not limited to, pace makers, subcutaneous sensing and delivery devices such as for diabetic therapy and skin surface mounted sensors). In addition, retinal activity sensors may be used to collect data during program segments or events, which may be specifically designed and configured to elicit responses under certain conditions.

Based on changes observed, the medication regimen is modified automatically using a treatment protocol or manually based on a doctor's instruction or changes in titration rates, and even dynamic media enabled content designed to improve the disease state.

Once an initial or amended treatment plan is created, the medication regimen may be employed manually by prescriptive means or, if the means of administering the medication is already coextensive with the individual's body, the regimen may be applied automatically. Examples of such coextensive means include, but are not limited to, passive devices such as skin patches and devices that are embedded subcutaneously to administer pharmaceuticals directly into the individual's biological system. Such devices may also be activated through a wireless or wired RF or infrared transmission devices located in the individual's living area or via media delivered sound and patterns. These devices may be further adapted to communicate with a remote system so that the passive devices may be triggered or modified remotely by a caregiver.

The treatment regimen, with or without additional instructions, may be sent to the individual by phone or manual delivering or directly to a display device 40 at the individual's home via an external source 46, such as satellite, cable or computer network service provider or via media content. Prescriptions may be sent through the same or similar system directly to a pharmacy 42, by the caregiver 44 or the individual, so that the individual can readily pick up the prescriptions or have them delivered. Display device 40 may be an analog or digital television, or desktop or hand held computer, or any other stationary or portable processor, with a suitable display screen (including but not limited to PDAs and iPODs, or other portable devices). If the individual has one or more of their pharmaceuticals administered through a programmable device 48 embedded in or on the individual's skin, the individual or the care giver may change the level of dosage using a wireless infra-red device. Other suitable means of administration may be used depending on the circumstances and devices available for a given patient.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for monitoring and treating individuals having a mental health disease comprising,
   one or more monitoring devices to collect individual daily activity data;
   a storage device for at least temporarily storing health-related information about one or more of said individuals wherein at least portion of said information comprises data on one or more of said individual's daily activities, and wherein said collected activity data comprises activity level data;
   a processor for analyzing said health related information to assess said individual's mental health; and
   a device for generating a treatment plan based at least in part on said individual's assessed mental health; and
   wherein one or more of the monitoring devices unobtrusively and automatically collects the activity data without active input by the individual.

2. The system of claim 1, further comprising a monitoring system for sensing one or more activities of said individual.

3. The system of claim 2, wherein said monitoring system comprises one or more actigraphy devices worn by the individual.

4. The system of claim 2, wherein the monitoring system comprises one or more of said sensors that continuously collects data over a twenty four hour period.

5. The system of claim 3, further comprising a means for transmitting data corresponding to said sensed activities to a remote location.

6. The system of claim 1, further comprising a means for transmitting at least part of said treatment plan to said individual.

7. The system of claim 6, wherein said means comprises a computer network.

8. The system of claim 1, wherein one or more of said activities is sleeping.

9. The system of claim 1, wherein said health related information comprises mental health information.

10. The system of claim 1, wherein said health related information comprises one or more physiological measurements.

11. The system of claim 1, further comprising a passive device for administering one or more medications to said individual, and a means for activating said passive device.

12. The system of claim 11, wherein said means for activating comprises a radio frequency or infrared signal.

13. The system of claim 1, wherein said activities may be selected from a group of activities consisting of: sleeping, activating or deactivating an in-home device, entering or leaving a living area of the individual, exercising, making sounds, physical movement by the individual, opening or closing a door or window, using a computer or other electronic digital devices, website usage, making financial relating transactions and selecting or using media.

14. A system for monitoring and treating individuals having a mental health disease comprising,
- a means for at least temporarily storing health-related information about one or more of said individuals wherein at least portion of said information comprises data on one or more of said individual's activities;
- a processor for analyzing said health related information to assess said individual's mental health;
- and a device for generating a treatment plan based at least in part on said individual's assessed mental health; and
- wherein said health related information further comprises personal credit related data.

15. The system of claim 1, wherein said assessment of mental health comprises an analysis of an absolute measure and a relative measure of mental acuity.

16. The system off claim 1, wherein said assessment of mental health comprises an analysis of depression.

* * * * *